United States Patent
SaNogueira et al.

(10) Patent No.: US 10,092,494 B2
(45) Date of Patent: Oct. 9, 2018

(54) SUNSCREEN COMPOSITIONS WITH IMPROVED WATER RESISTANCE OF UVA SUNSCREEN ACTIVE AGENTS

(71) Applicant: Edgewell Personal Care Brands, LLC, Chesterfield, MO (US)

(72) Inventors: James SaNogueira, Wesley Hills, NJ (US); Glenn Wiener, Ormond Beach, FL (US); Tao Zheng, New City, NY (US)

(73) Assignee: Edgewell Personal Care Brands, LLC., Chesterfield, MO (US)

( * ) Notice: Subject to any disclaimer, the term of this patent is extended or adjusted under 35 U.S.C. 154(b) by 0 days.

(21) Appl. No.: 15/264,003

(22) Filed: Sep. 13, 2016

(65) Prior Publication Data

US 2017/0189296 A1  Jul. 6, 2017

Related U.S. Application Data

(60) Provisional application No. 62/218,032, filed on Sep. 14, 2015.

(51) Int. Cl.

| A61K 8/58 | (2006.01) |
|---|---|
| A61K 8/04 | (2006.01) |
| A61K 8/31 | (2006.01) |
| A61K 8/34 | (2006.01) |
| A61K 8/35 | (2006.01) |
| A61K 8/37 | (2006.01) |
| A61K 8/40 | (2006.01) |
| A61K 8/67 | (2006.01) |
| A61K 8/81 | (2006.01) |
| A61K 8/895 | (2006.01) |
| A61K 8/97 | (2017.01) |
| A61Q 17/04 | (2006.01) |

(52) U.S. Cl.
CPC .............. *A61K 8/585* (2013.01); *A61K 8/046* (2013.01); *A61K 8/31* (2013.01); *A61K 8/34* (2013.01); *A61K 8/35* (2013.01); *A61K 8/37* (2013.01); *A61K 8/40* (2013.01); *A61K 8/678* (2013.01); *A61K 8/8105* (2013.01); *A61K 8/8152* (2013.01); *A61K 8/895* (2013.01); *A61K 8/97* (2013.01); *A61Q 17/04* (2013.01); *A61K 2800/30* (2013.01); *A61K 2800/54* (2013.01); *A61K 2800/594* (2013.01); *A61K 2800/87* (2013.01)

(58) Field of Classification Search
CPC .......... A61K 8/585; A61K 8/046; A61K 8/31; A61K 8/34; A61K 8/35; A61K 8/37; A61K 8/678; A61K 8/8152; A61K 8/895; A61K 8/97; A61K 2800/30; A61K 2800/54; A61K 2800/594; A61K 2800/87; A61L 8/40; A61Q 17/04
See application file for complete search history.

(56) References Cited

U.S. PATENT DOCUMENTS

| 2010/0266648 | A1* | 10/2010 | Ranade | A61K 8/06 424/401 |
|---|---|---|---|---|
| 2011/0301247 | A1* | 12/2011 | Hayakawa | A61K 8/891 514/772.3 |
| 2012/0189665 | A1* | 7/2012 | Susak | A61K 8/40 424/400 |
| 2014/0030198 | A1* | 1/2014 | Fares | A61K 8/34 424/60 |
| 2014/0186270 | A1* | 7/2014 | Suleiman | A61K 8/895 424/47 |
| 2014/0348757 | A1* | 11/2014 | Barrie | A61K 8/927 424/43 |
| 2015/0164773 | A1* | 6/2015 | Mou | A61K 8/88 424/59 |

* cited by examiner

*Primary Examiner* — Doan T Phan (57) ABSTRACT

Sunscreen compositions, products and methods that include at least one UVA sunscreen active agent, at least one UVB sunscreen active agent, and one or more water insoluble film forming polymers. The compositions, products and methods may further include one or more active or inactive cosmetic ingredients. The water insoluble film forming polymers synergistically affect the UVA and UVB sunscreen active agents, in particularly the UVA sunscreen active agents by significantly enhancing the water resistance of the UVA sunscreen active agents after water exposure as determined by the SPF and UVAPF values measured before and after water exposure.

19 Claims, 1 Drawing Sheet

SUNSCREEN COMPOSITIONS WITH IMPROVED WATER RESISTANCE OF UVA SUNSCREEN ACTIVE AGENTS

BACKGROUND OF THE INVENTION

1. Field of the Invention

The invention is directed to sunscreen compositions, and in particular, sunscreen compositions, products and methods having polymeric additives that improve water resistance of UVA actives contained therein.

2. Description of Related Art

Numerous sunscreens are currently available for protecting keratinous substrates such as skin and hair from ultraviolet (UV) solar radiation falling within both the UVB region (between 290 nm to 320 nm wavelengths) and the UVA region (between 320 nm and 400 nm wavelengths). Protection from UVA radiation is measured as a Protection Factor-UVA or PFA. Protection from UVB radiation is measured as a Sun Protection Factor or SPF. For instance, UVB radiation is absorbed by the epidermis layer causing erythema and cellular mutations, all of which damage the skin and underlying tissue. UVA radiation is even more damaging as it reaches deeper into the dermis layer. As such, UVA radiation may suppress immune functions, lead to loss of skin elasticity, promote premature signs of aging, as well as other undesirable health effects.

Currently available sunscreens can protect against both UVB and UVA radiation. However, water exposure and other adverse conditions such as sweat, can lead to diminished protection as the sunscreen can wash off the skin. Sunscreen manufacturers provide the consumer with a water resistance rating that is dictated by the 2011 U.S. Food & Drug Administration (FDA) Final Rule for Water Resistance wherein a sunscreen composition must meet the critical wavelength of 370 nm. However, the critical wavelength protocol does not take into account the efficacy of the sunscreen composition after exposure to real life conditions of water, sweat, salt water or pool water. Under the adverse conditions of water, salt, and/or chemicals, the sunscreen composition can lose its efficacy and provide limited or no protection to the consumer. Yet even though the critical wavelength is met, SPF is primarily a measure of protection against UVB radiation only. As such, a loss in protection against UVA radiation after a period of water immersion is not accounted for in efficacy testing.

The SPF of a sunscreen composition is determined by measuring the minimal erythema response on human skin treated with a sunscreen composition and untreated human skin on a single human subject. From these two measurements, the SPF is the ratio of the energy required to generate erythema on treated skin as compared to the energy required to generate erythema on untreated skin. While erythema is produced on human skin exposed to both UVB and UVA rays, UVB rays play a much greater role in their effect on skin. The erythemal action spectrum reveals that 99% of erythemal action resides in the UVB region and only 1% in the UVA region.

The marker used to measure UVA Protection Factor (UVAPF) is referred to as Persistent Pigment Darkening (PPD), which implements use of UVA rays only. PPD is based on the skin's response to the amount of UVA that enters the viable epidermis. One such test measures sunscreen-protected PPD skin to the unprotected PPD skin after exposure to UVA. However, these tests do not measure water resistance of UVA sunscreens.

Again, whether or not a sunscreen is deemed water resistant is based on the 2011 FDA Final Rule for water resistance. By relying on testing in which 99% of the effective energy dosage comes from UVB rays, and only 1% coming from UVA rays, currently available sunscreens incorrectly imply that both UVB and UVA protectants are "water resistant" to the same degree. As such, loss in protection against UVA radiation after a period of water immersion is not accounted for in sunscreens.

To overcome these deficiencies in the prior art, the present invention provides products, methods and sunscreen compositions with an increase in water resistance, namely, an increase in the water resistance of the UVA sunscreen active agents.

SUMMARY OF THE INVENTION

Bearing in mind the problems and deficiencies of the prior art, it is therefore an object of the present invention to provide sunscreen compositions, products, and methods thereof having broad spectrum of water resistance protection across both the UVB and UVA bands of the UV spectrum.

It is another object of the present invention to provide a sunscreen composition comprising: one or more UVA sunscreen active agents; one or more water insoluble film forming polymers, wherein the one or more water insoluble film forming polymers increase water resistance of the one or more UVA sunscreen active agents such that the level of retention of UVAPF values after water exposure, as determined by UVAPF values measured before and after water exposure, is greater than at least 60%, preferably greater than at least 70%, and most preferably greater than at least 80%.

The one or more UVA sunscreen active agents may comprise avobenzone; terephthalylidene dicamphor sulfonic acid; bis-disulizole disodium; disodium phenyl dibenzimidazole tetrasulfonate; diethylamino hydroxybenzoyl hexyl benzoate; bis-diethylamino hydroxybenzoyl benzoate; bis-benzoxazolylphenyl ethylhexylamino triazine, or combinations thereof. The sunscreen composition may further include one or more UVB sunscreen active agents comprising octocrylene; octinoxate; octisalate; homosalate; ensulizole; ethylhexyl triazone; enzacamene; amiloxate; diethylhexyl butamido triazine; benzylidene malonate polysiloxane; padimate-O; trolamine salicylate; cinoxate; p-aminobenzoic acid and derivatives thereof; or combinations thereof. The sunscreen composition may also include one or more sunscreen active agents that absorb both UVA and UVB radiation such as, for example, oxybenzone; meradimate; titanium dioxide; zinc oxide; bis-octrizole; bemotrizinol; drometrizole trisiloxane; sulisobenzone; dioxybenzone; or combinations thereof.

The one or more water insoluble film forming polymers may comprise monomers, copolymers, cross polymers and terpolymers of organo-silicone hybrids, biopolymers, acrylate, abietic acid derivatives, polyolefins, silicone resins, vinyl acetates, maleates, alkyl esters, long chain and short chain carboxylic acids, or combinations thereof. The one or more water insoluble film forming polymers may be present in a non-aqueous solvent. The non-aqueous solvent may comprise an alcohol, ether, fatty acid, silicone fluid, ester, hydrocarbon, fluorinated hydrocarbon, or combinations thereof. The one or more water insoluble film forming polymers may be present in an aqueous emulsion.

Preferably, the one or more water insoluble film forming polymers comprises of a terpolymer of vinyl acetate, mono-n-butyl maleate and isobornyl acrylate. Preferably, the terpolymer of vinyl acetate, mono-n-butyl maleate and isobornyl acrylate is dissolved in ethanol.

Preferably, the one or more water insoluble film forming polymers comprises of a silicone-organic hybrid material of crotonic acid/vinyl $C_{8-12}$ isoalkyl esters/VA/bis-vinyldimethicone crosspolymer. Preferably, the crotonic acid/vinyl $C_{8-12}$ isoalkyl esters/VA/bis-vinyldimethicone crosspolymer is dissolved in ethanol.

Preferably, the one or more water insoluble film forming polymers comprises of a biopolymer of shellac. Preferably, the shellac is dissolved in ethanol.

Preferably, the one or more water insoluble film forming polymers comprises of at least two water insoluble film forming polymers selected from the group consisting of trimethylsiloxysilicate, isododecane (and) acrylate/dimethicone copolymer, and acrylates/dimethicone copolymer (and) cyclopentasiloxane. Preferably, the at least two water insoluble film forming polymers are dissolved in one or both of isododecane and isohexadecane.

Preferably, the one or more water insoluble film forming polymers comprises of at least two water insoluble film forming polymers selected from the group consisting of methyl dihydroabietate, trimethylsiloxysilicate, hydrogenated polycyclopentadiene (and) isododecane, acrylates/dimethicone copolymer (and) cyclopentasiloxane, and combinations thereof. Preferably, the at least two water insoluble film forming polymers are dissolved in one or more solvents selected from the group consisting of isododecane, isohexadecane, disiloxane and diisopropyl adipate.

The sunscreen composition may further include one or more active or inactive cosmetic ingredients comprising of cosmetically acceptable carriers; oils; sterols; amino acids; moisturizers; powders; colorants; pigments; dyes; pH adjusters; perfumes; essential oils; cosmetic active ingredients; vitamins; essential fatty acids; sphingolipids; self-tanning compounds; fillers; emulsifying agents; antioxidants; surfactants; additional film formers; chelating agents; gelling agents; thickeners; emollients; humectants; minerals; viscosity and/or rheology modifiers; keratolytics; retinoids; hormonal compounds; alpha-keto acids; anti-mycobacterial agents; anti-fungal agents; anti-microbials; anti-virals; analgesics; anti-allergenic agents; H1 or H2 antihistamines; anti-inflammatory agents; anti-irritants; anti-neoplastics; immune system boosting agents; immune system suppressing agents; anti-acne agents; anesthetics; antiseptics; insect repellents; skin cooling compounds; skin protectants; skin penetration enhancers; exfoliants; lubricants; fragrances; staining agents; depigmenting agents; hypopigmenting agents; preservatives; stabilizers; pharmaceutical agents; photostabilizing agents; spherical powders; plant extracts; absorbents; salicylic acid; alpha and beta hydroxy acids; retinol and its derivatives; or any combination of the foregoing.

It is still yet another object of the invention to provide a sunscreen composition comprising: one or more UVA sunscreen active agents; one or more water insoluble film forming polymers comprising of monomers, copolymers, cross polymers and terpolymers of organo-silicone hybrids, biopolymers, acrylate, abietic acid derivatives, polyolefins, silicone resins, vinyl acetates, maleates, alkyl esters, long chain and short chain carboxylic acids, or combinations thereof; and one or more solvents comprising C2-10 alcohol, ether, fatty acid, silicone fluid, ester, hydrocarbon, fluorinated hydrocarbon, wherein said one or more water insoluble film forming polymers increase water resistance of said one or more UVA sunscreen active agents such that retention of UVAPF values after water exposure, as determined by UVAPF values measured before and after water exposure, is greater than at least 70%. Preferably, in one embodiment, the one or more water insoluble film forming polymers is present in an amount of up to 6 wt. % and the one or more solvents comprises ethanol. Preferably, in an alcohol-free embodiment, the one or more water insoluble film forming polymers is present in an amount of up to 6 wt. % and the one or more solvents comprises isododecane, isohexadecane, disiloxane, diisopropyl adipate, or a combination thereof.

It is another object of the present invention to provide a sunscreen composition comprising: one or more UVA sunscreen active agents; one or more UVB sunscreen active agents; one or more water insoluble film forming polymers, wherein the one or more water insoluble film forming polymers increase water resistance of the one or more UVA sunscreen active agents such that the level of retention of UVAPF values after water exposure, as determined by UVAPF values measured before and after water exposure, is greater than at least 60%.

It is yet another object of the present invention to provide a consumer packaged product comprising a sunscreen composition as disclosed herein.

It is still yet another object of the present invention to provide a method of absorbing ultraviolet radiation on a keratinous substrate comprising applying a sunscreen composition according to the embodiments disclosed herein to a keratinous substrate and subjecting the keratinous substrate to ultraviolet radiation.

BRIEF DESCRIPTION OF THE DRAWINGS

The features of the disclosure believed to be novel and the elements characteristic of the invention are set forth with particularity in the appended claims. The figures are for illustration purposes only and are not drawn to scale. The disclosure itself, however, both as to organization and method of operation, can best be understood by reference to the description of the preferred embodiment(s) which follows, taken in conjunction with the accompanying drawings in which:

DESCRIPTION OF THE PREFERRED EMBODIMENT(S)

The embodiments of the present invention can comprise, consist of, and consist essentially of the features and/or steps described herein, as well as any of the additional or optional ingredients, components, steps, or limitations described herein or would otherwise be appreciated by one of skill in the art. It is to be understood that all concentrations disclosed herein are by weight percent (wt. %.) based on a total weight of the composition unless otherwise indicated. Where appropriate, the INCI (International Nomenclature of Cosmetic Ingredients) name of ingredients/components is used.

A wide variety of sunscreen compositions contain both UVA active agents and UVB active agents. When these sunscreens are exposed to water it has been found that the UVA active agents wash off faster than their UVB counterparts. Some UVA active agents are water soluble such that upon exposure to water and/or sweat, they are washed away completely thereby exposing the user to harmful UVA rays.

Upon exposure to water and/or sweat, the efficacy of both the UVB and UVA active agents in the sunscreen compositions is depleted, unless there is re-application of the sunscreen composition. It has further been found that over user wear time, the UVA active agents and their corresponding protection from UVA radiation are lost at a higher rate and amount as compared to the UVB active agents therein. As such, using only the SPF as a measure of water resistance is insufficient to measure the level of protection from UVA radiation.

Table I is a list of sunscreen UVB and UVA active agents and their corresponding degrees of lipophilicity, measured as relative polarities (water (log P)).

TABLE I

Relative Lipophilicity of Sunscreen Chemicals Based Upon Their Calculated Partition Coefficients Between Octanol and Water

| CTFA name | Other names | Log P @25° C. |
|---|---|---|
| Glyceryl PABA | 1,2,3-Propanetriol, 1-(4-aminobenzoate) | −0.02 |
| Benzophenone-4 | Sulisobenzone | −1.51 |
| PABA | p-Amino benzoic acid | 0.74 |
| Benzophenone-8 | Dioxybenzone | 2.15 |
| Cinoxate | Ethoxyethyl methoxy cinnamate | 2.55 |
| Benzophenone-3 | Oxybenzone | 2.63 |
| Ethyl dihydroxypropyl PABA | Ethyl-4-bis(2-hydroxypropyl-aminobenzoate) | 2.84 |
| Amyl dimethyl PABA | Amyl dimethyl PABA | 4.53 |
| Butylmethoxy dibenzoylmethane | Butylmethoxy dibenzoylmethane | 4.86 |
| Menthyl anthranilate | Menthyl-O-aminobenzoate | 5.05 |
| Octyl salicylate | 2-Ethylhexyl salicylate | 5.30 |
| Homosalate | Homomenthyl salicylate | 5.61 |
| Octyl methoxy cinnamate | Ethylhexyl-p-methoxy cinnamate | 5.65 |
| Octocrylene | Octyl cyanodiphenylacrylate | 5.69 |
| Octyl dimethyl PABA | 2-Ethylhexyl-p-dimethyl aminobenzoate | 6.08 |

(See J. Soc. Cosmetic Chem., 38, 209-221, Table V (July/August 1987).)

Figure 1:
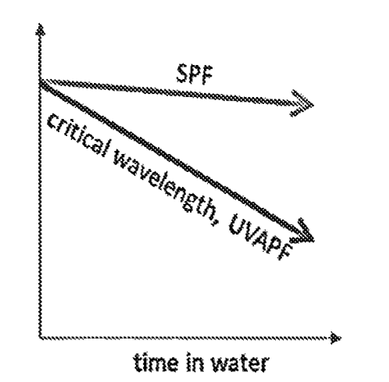
FIG. 1 is a schematic showing that upon exposure to water over time, the level of protection from UV radiation decreases at a faster rate for the UVA active agents in comparison with UVB active agents.

The data is listed in decreasing order of polarity (i.e., increasing log P values), and shows that the lipophilicity of sunscreens increase from water soluble (log P<1) to oil-soluble (log P>1). The table shows UVA active agents, e.g., avobenzone (butylmethoxy dibenzoylmethane), having lower polarities than their counterpart UVB active agents, e.g., octocrylene. Based on these polarities, UVA active agents tend to be more water soluble than UVB active agents. For instance, the polarities based on log P values show that avobenzone is more easily washed off than octocrylene such that upon exposure to water over time, the level of protection from UV radiation decreases at a faster rate for the UVA active agents in comparison with UVB active agents as shown in the schematic of FIG. 1.

In accordance with the various embodiments of the invention, sunscreen compositions, products, and methods are provided that unexpectedly increase water resistance of UVA active agents. In one or more embodiments, sunscreen compositions are provided having improved water resistance with greater retention of both UVB active agents and UVA active agents after exposure to water and/or sweat. The various sunscreen compositions of the invention include at least one or more polymer additives that synergistically affect the UVA active agents present in the compositions to unexpectedly retain a desirable level of protection against UVA radiation after exposure to water and/or sweat.

The present invention includes one or more polymeric additives in combination with various sunscreen UVB and UVA active agents to provide a sunscreen composition that has enhanced water resistance, and preferably enhanced water resistance of the UVA active agent, after water exposure. In one or more embodiments, the polymer additive is a water insoluble film forming polymer. The various water insoluble film forming polymers suitable for use in the present invention provide the resultant sunscreen composition with preferably greater than 60% retention, more preferably greater than 70% retention, and most preferably greater than 80% retention of the UVAPF levels after water exposure.

The sunscreen compositions of the invention may include various sunscreen active agents. Suitable sunscreen actives that may be used in sunscreen compositions of the invention include, but are not limited to, one or more of the following: p-aminobenzoic acid (PABA) and derivatives thereof; avobenzone (also known as butylmethoxy dibenzoylmethane); 2,4-dihydroxybenzophenone; 2,2',4,4'-tetrahydroxybenzophenone; oxybenzone; sulisobenzone; sulisobenzone sodium; 2,2'-dihydroxy-4,4'-dimethoxybenzophenone; 5-chloro-2-hydroxybenzophenone; dioxybenzone; sodium 2,2'-dihydroxy-4,4'-dimethoxybenzophenone-5,5'-disulfonate; 2-hydroxy-4-methoxy-4'-methyl-benzophenone; octabenzone; ethyl dihydroxypropyl-p-aminobenzoate; glyceryl-p-aminobenzoate; homosalate; methyl anthranilate; octocrylene; octyl dimethyl-p-aminobenzoate; isoamyl-p-methoxycinnamate; octyl methoxycinnamate; octyl salicylate; triethanolamine salicylate; 3-(4-methylbenzylidene) camphor; enzacamene; phenylbenzimidazole sulfonic acid; methylene bis-benzotriazolyl tetramethylbutyl phenol; 4-isopropyldibenzoylmethane; octisalate; bis-ethylhexyloxyphenol methoxyphenyl triazine; 4-isopropyl-dibenzoyl-methane; metal oxides such as zinc oxide or titanium dioxide; terephthalylidene dicamphor sulfonic acid (also known as ecamsule); drometrizole trisiloxane; diethylhexylbutamido triazone; ethylhexyl triazone; cinoxate; ensulizole; bis-disulizole disodium; diethylamino hydroxybenzoyl hexylbenzoate; or combinations thereof. It should be appreciated and understood that the present sunscreen compositions may include one or more other known ingredients suitable for use in absorbing, scattering and/or deflecting UVA and UVB radiation on a keratinous substrate.

Preferred sunscreen active agents that absorb and provide protection in the UVB spectrum include, but are not limited to, octocrylene; octinoxate; octisalate; homosalate; ensulizole; ethylhexyl triazone; enzacamene; amiloxate; diethylhexyl butamido triazine; benzylidene malonate polysiloxane; padimate-O; trolamine salicylate; cinoxate; PABA; or combinations thereof.

Preferred sunscreen active agents that absorb and provide protection in the UVA spectrum include, but are not limited to, avobenzone; terephthalylidene dicamphor sulfonic acid; bis-disulizole disodium; disodium phenyl dibenzimidazole tetrasulfonate; diethylamino hydroxybenzoyl hexylbenzoate; bis-diethylamino hydroxybenzoyl benzoate; bis-benzoxazolylphenyl ethylhexylamino triazine, or combinations thereof.

Preferred sunscreen active agents that absorb and provide both broad UVA and UVB protection include, but are not limited to, oxybenzone; meradimate; titanium dioxide; zinc oxide; bis-octrizole; bemotrizinol; drometrizole trisiloxane; sulisobenzone; dioxybenzone, or combinations thereof.

The various sunscreen active agents of the instant sunscreen formulations may be present in an amount of about 0.01 wt. % to about 40.0 wt. %, based on a total weight of the sunscreen composition. The individual weight percentage amounts and types of sunscreen active agents of the instant compositions will vary depending upon the desired sun protection factor (SPF) and the UVA Protection Factor (UVAPF). The higher the SPF and UVAPF, the greater the total amount of sunscreen active agents. The one or more sunscreen active agents may be present in an amount of about 3.0 wt. % to about 30.0 wt. % to achieve a SPF of about 15 to about 200 and more, based on a total weight of the sunscreen composition. The one or more additional sunscreen agents may be present in an amount of about 3.0 wt. % to about 25.0 wt. %, based on a total weight of the sunscreen composition, for a lower SPF.

The sunscreen compositions further include at least one or more polymer additives that enhance the water resistance of the sunscreen composition and, in particular, the UVA active agents after exposure to water. The one or more polymer additives have a synergistic effect on the sunscreen active agents, particularly on the UVA active agents, enhancing the water resistance during water activity or sweat. The one or more polymer additives suitable for use in the invention provide high retention rates of UVAPF values of greater than at least 60%, more preferably greater than at least 70%, and most preferably greater than at least 80%, after water exposure as determined by UVAPF values measured before and after water exposure.

The one or more polymer additives comprise water insoluble film forming polymers. The water insoluble film forming polymers comprise, but are not limited to, monomers, copolymers, cross polymers and/or terpolymers of organo-silicone hybrids, silicone resins, biopolymers, acrylates, abietic acid derivatives, polyolefins, vinyl acetates, maleates, alkyl esters, long chain and short chain carboxylic acids, and combinations thereof.

Exemplary of the water insoluble film forming polymers as a terpolymer is vinyl acetate (VA)/butyl maleate/isobornyl acrylate copolymer commercially available as ADVANTAGE™ Plus from Ashland Inc., Covington, Kentucky, as a 50% ethanolic solution. Exemplary of an organo-silicone hybrid is ethanol (and) crotonic acid/vinyl $C_{8-12}$ isoalkyl esters/VA/bis-vinyldimethicone crosspolymer commercially available as BELSIL® P1101 available from Wacker Chemie AG, Laramie, Wyo. Exemplary of biopolymers is shellac commercially available as POLY-SOLEIL® from Mantrose-Haeuser Co., Inc., Westport, Conn. Exemplary acrylate copolymers useful as water insoluble film forming polymers are isododecane (and) acrylate/dimethicone copolymer such as, KP 550, or acrylates/dimethicone copolymer (and) cyclopentasiloxane such as KP 545, both commercially available from Shin-Etsu Chemical Co., Ltd., Japan. An exemplary abietic acid derivative is methyl dihydroabietate, such as MERISTANT® 101L commercially available from Essential Ingredients, Lawrenceville, Ga. Exemplary of a polyolefinic water insoluble film forming polymer useful in the present invention is hydrogenated polycyclopentadiene (and) isododecane commercially available as KOBOGUARD® 5400 IDD available from Kobo Products, Inc., South Plainfield, N.J., sold as an isododecane solution. Exemplary of a silicone resin useful in the present invention is MQ Solid Resin commercially available from Dow Corning Corporation, Midland, Mich.

The water insoluble film forming polymers may be provided in amounts ranging from 0.2 wt. % to about 15 wt. %, of the total weight of the sunscreen composition, preferably from about 1.0 wt. % to about 10 wt. %, and most preferably from about 1.5 wt. % to about 6.0 wt. % (of the total weight of the sunscreen composition). While the water insoluble film forming polymers are known film formers, it is unexpected that the addition of these polymeric additives to a sunscreen composition would enhance water resistance of both UVB and UVA active agents, and significantly maximize the water resistance of UVA active agents such that the level of retention of the UVAPF values after water exposure is greater than at least 60%.

In preparing the sunscreen compositions of the present invention, the water insoluble film forming polymers are provided in solution in one phase, and added to another phase containing the sunscreen active agents. These water insoluble film forming polymers are preferably dissolved or suspended in a non-aqueous solvent although sunscreen compositions utilizing emulsions involving aqueous phases are also contemplated herein. Such non-aqueous solvents include, but are not limited to, $C_2$ to $C_{10}$ alcohols, ethers, fatty acids, silicone fluids, esters, hydrocarbons, and fluorinated hydrocarbons. Some of the commercially available water insoluble film forming polymers are sold as a solution in a non-aqueous solvent, for example, ADVANTAGE Plus, KOBOGUARD, and others disclosed herein.

In some embodiments, the sunscreen composition includes sunscreen active agents, and a synergistic combination of a water insoluble film forming polymer comprising 3 wt. % VA/butyl maleate/isobornyl acrylate copolymer and the solvent is ethanol.

In some embodiments, the sunscreen composition includes sunscreen active agents, and a synergistic combination of a water insoluble film forming polymer comprising 3 wt. % crotonic acid/vinyl $C_{8-12}$ isoalkyl esters/VA/bis-vinyldimethicone crosspolymer and the solvent is ethanol.

In some embodiments, the sunscreen composition includes sunscreen active agents, and a synergistic combination of a water insoluble film forming polymer comprising 1.5 wt. % shellac and the solvent is ethanol.

In some embodiments, the sunscreen composition includes sunscreen active agents, and a synergistic combination of a water insoluble film forming polymer comprising 3 wt. % trimethylsiloxysilicate, 3 wt. % isododecane (and) acrylate/dimethicone copolymer and the solvents are isododecane and isohexadecane.

In some embodiments, the sunscreen composition includes sunscreen active agents, and a synergistic combination of a water insoluble film forming polymer comprising 0.5 wt. % trimethylsiloxysilicate, 0.2 wt. % acrylate/dimethicone copolymer (and) cyclopentasiloxane and the solvent is isododecane.

In some embodiments, the sunscreen composition includes sunscreen active agents, and a synergistic combination of a water insoluble film forming polymer comprising 3 wt. % trimethylsiloxysilicate, 3 wt. % acrylate/dimethicone copolymer (and) cyclopentasiloxane and the solvents are isododecane and isohexadecane.

In some embodiments, the sunscreen composition includes sunscreen active agents, and a synergistic combination of a water insoluble film forming polymer comprising 3 wt. % trimethylsiloxysilicate, 3 wt. % acrylate/dimethicone copolymer (and) cyclopentasiloxane and the solvents are isododecane, isohexadecane, and disiloxane.

In some embodiments, the sunscreen composition includes sunscreen active agents, and a synergistic combination of a water insoluble film forming polymer comprising 2 wt. % trimethylsiloxysilicate, 1 wt. % methyl dihydroabietate and the solvents are isododecane, isohexadecane, and disiloxane.

In some embodiments, the sunscreen composition includes sunscreen active agents, and a synergistic combination of a water insoluble film forming polymer comprising 2 wt. % trimethylsiloxysilicate, 1 wt. % methyl dihydroabietate and the solvents are isododecane, diisopropyl adipate, and disiloxane In some embodiments, the sunscreen composition includes sunscreen active agents, and a synergistic combination of a water insoluble film forming polymer comprising 2 wt. % polycyclopentadiene (and) isododecane and the solvents further include isohexadecane and disiloxane.

In some embodiments, the sunscreen composition includes sunscreen active agents, and a synergistic combination of a water insoluble film forming polymer comprising 2 wt. % methyl dihydroabietate and the solvents are isododecane, isohexadecane and disiloxane.

In some embodiments, the sunscreen composition includes sunscreen active agents, and a synergistic combination of a water insoluble film forming polymer comprising 4 wt. % polycyclopentadiene (and) isododecane and the solvents further include isohexadecane and disiloxane.

In some embodiments, the sunscreen composition includes sunscreen active agents, and a synergistic combination of a water insoluble film forming polymer comprising 4 wt. % methyl dihydroabietate and the solvents are isododecane, isohexadecane and disiloxane.

While the invention has been described in relation to two phases of the resultant sunscreen compositions (i.e., Phase A and Phase B), it should be appreciated and understood that multiple phases of compositions may be prepared and ultimately mixed to provide the various sunscreen compositions of the invention having improved UVA water resistance. In accordance with one or more embodiments, the ingredients or constituents of a first phase containing the sunscreen active agents, with or without other cosmetic ingredients, are provided into a vessel and mixed under temperatures of about 70° C. to 75° C. until a uniform or clear solution is rendered. This solution is cooled to a temperature of about 30° C. with continuous mixing. In a separate vessel, the water-insoluble polymeric additives are dissolved in a solvent and mixed at a temperature of about 30° C. until a homogeneous water insoluble polymer additive second phase solution is rendered. The first and second phases may then be mixed together until a homogenous solution is obtained. Optionally, preservatives, such as phenoxyethanol as an example only, may be added to the sunscreen formulation, and the composition cooled, preferably to room temperature. Adjustments to the pH of the final sunscreen composition may also be made at this time.

The sunscreen composition may further include one or more active or inactive cosmetic ingredients, such as, but not limited to, cosmetically acceptable carriers; oils; sterols; amino acids; moisturizers; powders; colorants (including pigments and/or dyes); pH adjusters; perfumes; essential oils; cosmetic active ingredients; essential fatty acids; sphingolipids; self-tanning compounds such as dihydroxyacetone (DHA) and erythruloses; fillers; emulsifying agents; antioxidants; surfactants; additional film formers; chelating agents; gelling agents; thickeners; emollients; humectants; minerals; viscosity and/or rheology modifiers; keratolytics; retinoids; hormonal compounds; alpha-keto acids; anti-mycobacterial agents; anti-fungal agents; anti-microbials; antivirals; analgesics; anti-allergenic agents; H1 or H2 antihistamines; anti-inflammatory agents; anti-irritants; anti-neoplastics; immune system boosting agents; immune system suppressing agents; anti-acne agents; anesthetics; antiseptics; insect repellents; skin cooling compounds; skin protectants; skin penetration enhancers; exfoliants; lubricants; fragrances; staining agents; depigmenting agents; hypopigmenting agents; preservatives; stabilizers; pharmaceutical agents; photostabilizing agents; spherical powders; plant extracts; absorbents; salicylic acid; alpha and beta hydroxy acids; vitamins including vitamins A, C, and E; retinol and its derivatives; or any combination of the foregoing. It should be appreciated and understood that this list is not limiting, and that various other active or inactive ingredients may be used in the present sunscreen formulations.

Testing was performed on the sunscreen compositions of the invention. In vitro water resistance testing was performed on compositions of the invention and the results analyzed using both high performance liquid chromatography (HPLC) and spectroscopic analysis, as well as in vivo water resistance using the methodology disclosed in the 2011 FDA Final Rule for Water Resistance to show the improved water resistance of the inventive compositions. In the spectroscopic analysis, absorbance retention rates across both the UVB and UVA regions were obtained using an ultraviolet spectrophotometer (Ultraviolet Transmittance Analyzer Model UV-2000 available from Labsphere Inc., North Sutton, N.H.) and presented in the below tables. In the spectroscopic analysis, an amount of the sunscreen compositions was uniformly applied to VITRO-SKIN®, commercially available from IMS, Inc., Portland, Me., by finger with a pre-saturated finger cot. The coated plate was air-dried (e.g., for about 15 minutes) and then placed inside the ultraviolet spectrophotometer. Spectral absorbance measurements were taken at four randomly selected points. The readings were recorded by the spectrophotometer and the calculation of the SPF value was made based on the following equation:

$$SPF_{in\ vitro} = \frac{\int_{\lambda=290}^{\lambda=400} E(\lambda) \times I(\lambda) \times d\lambda}{\int_{\lambda=290}^{\lambda=400} E(\lambda) \times I(\lambda) \times 10^{-A_0(\lambda)} \times d\lambda}$$

with the use of built-in software: UV-2000 application Version 1.1.0.0, wherein $E(\lambda)$ is the erythemal action spectrum, $I(\lambda)$ is the spectral irradiance received from the UV source, and $A_0(\lambda)$ is the mean monochromatic absorbance of the test product layer before UV exposure, and $d\lambda$ is the wavelength step (1 nm). Averages of the four readings are shown in the below tables as the percent of UVB absorbance retention based on the measured SPF before and after water exposure.

Based on the ultraviolet spectrophotometer analysis and readings, the UVAPF in vitro water resistance was measured, and UVA absorbance retention percentage was obtained using measurements before water immersion and after water immersion in accordance with the 2011 FDA Final Rule for Very Water Resistance (VWR) based on eighty minutes of submersion. The UVA absorbance retention percentage was calculated based on the following equation:

$$UVA\ \text{Absorbance Retention \%} = \frac{(UVA\ \text{Absorbance})_{VWR}}{(UVA\ \text{Absorbance})_{Static}} \times 100\%$$

Concentration of UV active agents on a substrate as determined by HPLC was also performed on samples of the inventive compositions. Test samples were applied in duplicate onto a substrate followed by water immersion of one substrate containing sample over one or more timed intervals. The test sample was extracted from both the immersed substrate and the un-immersed substrate and HPLC assay was conducted on the diluent from each substrate. The difference in before and after measurements provides the amount of each UV active agent lost due to water exposure. The in vitro HPLC sunscreen retention percentages of the following active agents: octocrylene, avobenzone, octisalate and homosalate, after water exposure are discussed below.

Sunscreen compositions of the invention were also tested using in vivo methods to show the enhanced retention rates of the UVB and UVA active agents in the inventive compositions after water exposure. Table II below shows in vivo water resistance retention percentages across both the UVB and UVA spectrum for Examples 1 to 3. These in vivo water resistance tests confirm that the water insoluble film forming polymers suitable in the present invention provide enhanced water resistance of the sunscreen composition, and significantly maximized the water resistance of UVA active agents wherein greater than at least 60%, more preferably greater than at least 70%, and most preferably greater than at least 80%, UVA active agents are retained on the substrate surface after water exposure, or even after exposure to sweat.

Various sunscreen formulations in accordance with the invention are set forth in the following examples. It should be appreciated and understood that these formulations may be modified and/or added to with various constituents at different concentrations while still falling within the scope of the invention.

EXAMPLES

In all examples, the inventive compositions contained the following sunscreen active agents: homosalate (10 wt. %), octocrylene (6 wt. %), octisalate (5 wt. %), avobenzone (3 wt. %); and the following cosmetic ingredients: caprylyl glycol (0.70 wt. %), tocopheryl acetate (0.01 wt. %), and aloe barbadensis leaf extract (and) mineral oil (0.01 wt. %), all based on a total weight of the sunscreen composition.

Examples 1 to 3 are inventive anhydrous formulations wherein the water insoluble film forming polymers are dissolved in an alcohol. These examples were formulated as aerosols. The first phase included the UVA and UVB components as well as the above mentioned cosmetic ingredients. The first phase constituents were provided into a beaker neat, heated to about 70° C. to 75° C. with mixing until a clear solution was obtained. The solution was then allowed to cool to a temperature of about 30° C. with continuous mixing.

The second phase constituents included at least one of the following water insoluble film forming polymers: VA/butyl maleate/isobornyl acrylate copolymer; crotonic acid/vinyl $C_{8-12}$ isoalkyl esters/VA/bis-vinyldimethicone crosspolymer, or shellac. These water insoluble film forming polymers were combined with an alcohol solvent, in particular, ethanol. The water insoluble film forming polymer and alcohol solvent were provided into and mixed in a separate beaker at a temperature of about 30° C. until a homogeneous solution was obtained. The two phases were combined until a clear solution was obtained.

Referring to Table II below, different alcohol-based sunscreen compositions were tested for UVB and UVA retention rates. These results showed the enhanced UVB and UVA retention rates due to use of the water insoluble film forming polymer additives in one or more embodiments of alcohol based sunscreen compositions of the invention.

TABLE II

Alcohol Based Sunscreen Compositions

| | Example | | |
|---|---|---|---|
| | 1 | 2 | 3 |
| Polymeric Additive | VA/butyl maleate/ isobornyl acrylate copolymer* | crotonic acid/ vinyl $C_{8-12}$ isoalkyl esters/VA/bis-vinyldimethicone crosspolymer+ | shellac^ |
| | 3 wt. % | 3 wt. % | 1.5 wt. % |
| Ethanol | 72.28 wt. % | 72.28 wt. % | 73.78 wt. % |
| in vitro Water Resistance Test Data by UV Spectrophotometer | | | |
| retention of UVB absorbance | 61.81% | 93.41% | 119.37% |
| retention of UVA absorbance | 47.09% | 83.50% | 118.37% |
| in vivo Water Resistance Test Data | | | |
| retention of SPF | 88.09% | 89.94% | 87.42% |
| retention of UVAPF | 73.31% | 86.36% | 95.29% |
| Sunscreen Active Agent Retention (HPLC) | | | |
| homosalate | 72.59% | 82.94% | 92.01% |
| octocrylene | 84.52% | 90.30% | 94.19% |
| octisalate | 66.38% | 82.06% | 92.37% |
| avobenzone | 25.42% | 66.81% | 75.91% |

*commercially available as ADVANTAGE Plus
+commercially available as BELSIL P1101
^commercially available as POLY-SOLEIL The in vitro water resistance test results analyzed by UV spectrophotometer, and the in vivo water resistance test results of Examples 1 to 3 are shown in Table II. While these results show that selected water insoluble film forming polymers may show more retention of UVB and UVA in one test method as compared to another, the unexpected advantage is that all three water insoluble film forming polymers show enhanced water resistance of both UVB and UVA active agents in one test method or the other, and importantly, a significant enhancement (e.g., preferably at least 60% or greater retention) in water resistance of UVA active agents not found in conventional sunscreen formulations. For example, while the in vitro water resistance data of Example 1 shows a modest retention of UVA absorbance, the in vivo test data shows a significant retention of UVA absorbance that was not predicted by the in vitro data. In vivo test results in Examples 2 and 3 show the retention of UVAPF on par with SPF not found in conventional sunscreen compositions due to the addition of the water insoluble film forming polymers.

HPLC results show the effects of the individual water insoluble film forming polymers of Examples 1 to 3 on different UVB and UVA active agents. Examples 2 and 3 show a broader spectrum coverage with enhanced water resistance of different UVB and UVA active agents after water exposure. For instance, the HPLC results show that Examples 2 and 3 retain the UVA active avobenzone to a significantly greater extent as compared to Example 1, which is most similar to commercially available sunscreen compositions.

In other examples of the present invention, alcohol-free compositions were made in accordance with the various embodiments of the invention. Examples 4 to 13 shown in Table III show different alcohol-free compositions having the following sunscreen actives agents: 10% homosalate, 5% octisalate, 6% octocrylene, and 3% avobenzone, with avobenzone providing the bulk of protection against UVA radiation. Like that of the alcohol based formulations, these compositions may also be made using one or more phases, with a first phase including one or more UVA and UVB active agents and other cosmetic active or inactive ingredients and a second phase containing one or more of the water insoluble film forming polymers. These examples may include one, two, or possibly more, water insoluble film forming polymers dissolved in one or more, preferably at least two, organic solvents to provide a water insoluble film forming polymers second phase that is combined with the sunscreen active agent phase to render the present sunscreen formulations having enhanced UVB and/or UVA water resistance.

TABLE III

Alcohol-Free Sunscreen Formulations

| | Example | | | | |
|---|---|---|---|---|---|
| | 4 | 5 | 6 | 7 | 8 |
| Polymer Additive #1 | trimethylsiloxysilicate[λ] 3 wt. % | trimethylsiloxysilicate 0.5 wt. % | trimethylsiloxysilicate 3 wt. % | trimethylsiloxysilicate 3 wt. % | trimethylsiloxysilicate 2 wt. % |
| Polymer Additive #2 | isododecane (and) acrylate/dimethicone copolymer[µ] 3 wt. % | acrylate/dimethicone copolymer (and) cyclopentasiloxane[✓] 0.2 wt. % | acrylate/dimethicone copolymer (and) cyclopentasiloxane 3 wt. % | acrylate/dimethicone copolymer (and) cyclopentasiloxane 3 wt. % | methyl dihydro abietate 1 wt. % |
| Solvent #1 | 49.3 wt. % IDD | 74.6% IDD | 49.3 wt. % IDD | 20 wt. % IDD | 20 wt. % IDD |
| Solvent #2 | 20 wt. % IHD | — | 20 wt. % IHD | 20 wt. % IHD | 20 wt. % IHD |
| Solvent #3 | — | — | — | 29.3 wt. % DS | 32.3 wt. % DS |
| in vitro Water Resistance Test Results (UV Spectrophotometer) | | | | | |
| retention of UVB absorbance | 94% | 109% | 94% | 92% | 92% |
| retention of UVA absorbance | 73% | 104% | 90% | 71% | 77% |

| | Example | | | | |
|---|---|---|---|---|---|
| | 9 | 10 | 11 | 12 | 13 |
| Polymer Additive #1 | trimethylsiloxysilicate 2 wt. % | polycyclopentadiene (and) isododecane[Δ] 2 wt. % | methyl dihydro abietate[¥] 2 wt. % | polycyclopentadiene (and) isododecane 4 wt. % | methyl dihydro abietate 4 wt. % |
| Polymer Additive #2 | methyl dihydro abietate 1 wt. % | — | — | — | — |
| Solvent #1 | 20 wt. % IDD | 42 wt. % IDD | 42 wt. % IDD | 20 wt. % IDD | 20 wt. % IDD |
| Solvent #2 | 20 wt. % DIPA | 19 wt. % IHD | 19 wt. % IHD | 20 wt. % IHD | 20 wt. % IHD |
| Solvent #3 | 32.3 wt. % DS | 12.3 wt. % DS | 12.3 wt. % DS | 31.3 wt. % DS | 31.3 wt. % DS |
| in vitro Water Resistance Test Results (UV Spectrophotometer) | | | | | |
| retention of UVB absorbance | 82% | 58% | 38% | 66% | 51% |
| retention of UVA absorbance | 64% | 42% | 19% | 51% | 39% |

IDD = isododecane;
IHD = isohexadecane;
DS = disiloxane;
DIPA = diisopropyl adipate
[^] commercially available as MQ-1600 Solid Resin
[Δ] commercially available as KOBOGUARD 5400 IDD
[¥] commercially available as MERISTANT 101L
[µ] commercially available as KP 550
[✓] commercially available as KP 545

In vitro water resistance tests were analyzed using a UV spectrophotometer on Examples 4 to 13 and presented in Table III above. These results show the retention percent of both the UVB absorbance and UVA absorbance of the sunscreen compositions of Examples 4 to 13. Each of the exemplary sunscreen compositions in Examples 4 to 9 exhibit high retention rates of greater than at least 60%, more preferably greater than at least 70%, and most preferably greater than at least 80%, of the UVA and UVB absorbance after water exposure measured using the UV spectrophotometer. A synergistic effect of more than one water insoluble film forming polymers with one or more solvents is also evident noting the high retention of UVA active agents after water exposure.

Examples 7 to 9 include one or more water-insoluble film forming polymers in combination with at least three different solvents to render the sunscreen compositions of the invention. Thus, one of ordinary skill in the art can appreciate that in some embodiments, more than two water-insoluble film forming polymers may be combined with more, or less, than three different solvents. Examples 7 to 9 provide enhanced water resistance of both the UVB and UVA active agents.

Examples 10 to 13 include one water-insoluble polymeric additive in combination with at least three different solvents. These results illustrate the preference in one or more embodiments of the invention in utilizing combinations of water-insoluble polymeric additives when using combinations of solvents.

Commercial sunscreen compositions were evaluated as shown in Table IIA. The UVA sunscreen active agents are shown to wash off the skin after water immersion at much higher rates than those found in the inventive compositions disclosed herein.

TABLE IIA

Comparative Data

| Example | CT | BB1 |
|---|---|---|
| in vivo Water Resistance Test Data | | |
| retention of SPF | | 94% |
| retention of UVAPF | | 48% |
| Sunscreen Active Agent Retention (HPLC) | | |
| UVB actives | 75% | |
| UVA actives | 58% | |

CT = Coppertone ® Clearly Sheer SPF 50+
BB1 = Banana Boat Clear Spray SPF 50

It has been found that the various sunscreen compositions of the present invention are more robust after water exposure providing consumers with lasting UVA protection and UVB protection. The synergistic effects of the various water-insoluble film forming polymers (either singularly or in combinations of two or more) suitable for use in the invention with UVB and UVA sunscreen active agents provides increased water resistance of such active agents when exposed to water and/or sweat. One of skill in the art will understand how to formulate the inventive sunscreen compositions into suitable consumer packaged products.

In accordance with the various embodiments, the inventive sunscreen compositions may be formulated as continuous aerosol sprays, such as the alcohol-based aerosol sprays in Examples 1 to 3, oil-in-water (O/W) or water-in-oil (W/O) emulsions, anhydrous topical formulations, lotions, creams, sprays, etc., as show in Examples 4 to 13. It has unexpectedly been found that the water insoluble film forming polymers suitable for use in the invention provide sunscreen compositions having improved water resistance of both UVB and UVA active agents, with significant water resistance enhancement of the UVA active agents. UVA active agents are retained on a keratinous substrate to at least 60% or greater retention after exposure to water and/or sweat. As such, the sunscreen compositions of the invention decrease the loss of UVA active agents on the skin, and thereby increase protection from UV radiation between 320 nm and 400 nm wavelengths, after water wash, water immersion, swimming, sweating, and the like.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. An anhydrous topical sunscreen composition comprising
   one or more sunscreen active agents including UVA sunscreen active agents;
   at least two water insoluble film forming polymers selected from the group consisting of (i) trimethylsiloxysilicate, alone or in combination with (ii) acrylate/dimethicone copolymer, (iii) methyl dihydroabietate, and combinations thereof; and
   a first solvent comprising isododecane, and
   a second solvent comprising isohexadecane, disiloxane, diisopropyl adipate, or a combination thereof, wherein said at least two water insoluble film forming polymers are dissolved in the first and second solvents, and
   wherein the combination of said one or more water insoluble film forming polymers and said first and second solvents increase water resistance of UVA sunscreen active agents such that retention of UVAPF values after water exposure, as determined by UVAPF values measured before and after water exposure, is greater than at least 70%.

2. The anhydrous topical sunscreen composition of claim 1, wherein said at least two water insoluble film forming polymers are dissolved in isododecane and isohexadecane.

3. The anhydrous topical sunscreen composition of claim 1 wherein said at least two water insoluble film forming polymers are dissolved in three solvents selected from the group consisting of isododecane, isohexadecane, disiloxane and diisopropyl adipate.

4. The anhydrous topical sunscreen composition of claim 1 wherein said sunscreen composition includes one or more UVB sunscreen active agents, and said UVA and UVB sunscreen active agents are present in an amount of about 0.01 wt. % to about 40.0 wt. %, based on a total weight of the sunscreen composition.

5. The anhydrous topical sunscreen composition of claim 4 wherein said sunscreen active agents are present in an amount of about 3.0 wt. % to about 30.0 wt. %.

6. The anhydrous topical sunscreen composition of claim 1 wherein said sunscreen composition further includes one or more active or inactive cosmetic ingredients.

7. The anhydrous topical sunscreen composition of claim 6 wherein said one or more active or inactive cosmetic ingredients comprise cosmetically acceptable carriers; oils; sterols; amino acids; moisturizers; powders; colorants; pigments; dyes; pH adjusters; perfumes; essential oils; cosmetic active ingredients; vitamins; essential fatty acids; sphingolipids; self-tanning compounds; fillers; emulsifying agents; antioxidants; surfactants; additional film formers; chelating agents; gelling agents; thickeners; emollients; humectants; minerals; viscosity and/or rheology modifiers; keratolytics; retinoids; hormonal compounds; alpha-keto acids; anti-mycobacterial agents; anti-fungal agents; anti-microbials; antivirals; analgesics; anti-allergenic agents; H1 or H2 antihistamines; anti-inflammatory agents; anti-irritants; anti-neoplastics; immune system boosting agents; immune system suppressing agents; anti-acne agents; anesthetics; antiseptics; insect repellents; skin cooling compounds; skin protectants; skin penetration enhancers; exfoliants; lubricants; fragrances; staining agents; depigmenting agents; hypopigmenting agents; preservatives; stabilizers; pharmaceutical agents; photostabilizing agents; spherical powders; plant extracts; absorbents; salicylic acid; alpha and beta hydroxy acids; retinol and its derivatives; or any combination of the foregoing.

8. The anhydrous topical sunscreen composition of claim 1, wherein said at least two water insoluble film forming polymers are present in an amount of up to 10 wt. %.

9. The anhydrous topical sunscreen composition of claim 1, wherein said at least two water insoluble film forming polymers comprise (i) trimethylsiloxysilicate and (ii) methyl dihydroabietate present in an amount of up to 6 wt. %.

10. The anhydrous topical sunscreen composition of claim 1, wherein said at least two water insoluble film forming polymers comprise (i) trimethylsiloxysilicate and (ii) acrylate/dimethicone copolymer present in an amount of up to 6 wt. %, and said solvents comprise isododecane and isohexadecane.

11. The anhydrous topical sunscreen composition of claim 1, wherein said at least two water insoluble film forming polymers comprise (i) trimethylsiloxysilicate and (ii) acrylate/dimethicone copolymer present in an amount of up to 6 wt. %, and at least two solvents comprises isododecane, isohexadecane, or disiloxane.

12. A consumer packaged product comprising an anhydrous topical sunscreen composition of claim 1.

13. A method of absorbing ultraviolet radiation on a keratinous substrate comprising applying a sunscreen composition according to claim 1 to a keratinous substrate and subjecting the keratinous substrate to ultraviolet radiation.

14. A method of absorbing ultraviolet radiation on a keratinous substrate comprising applying a sunscreen composition according to claim 8 to a keratinous substrate and subjecting the keratinous substrate to ultraviolet radiation.

15. A method of absorbing ultraviolet radiation on a keratinous substrate comprising applying an alcohol-free sunscreen composition according to claim 10 to a keratinous substrate and subjecting the keratinous substrate to ultraviolet radiation.

16. An anhydrous topical sunscreen composition comprising
   sunscreen actives including UVA sunscreen actives;
   at least two water insoluble film forming polymers selected from the group consisting of trimethylsiloxysilicate, acrylate/dimethicone copolymer, and methyl dihydroabietate; and
   a solvent mixture consisting essentially of isododecane in combination with one or more selected from the group consisting of isohexadecane, disiloxane, diisopropyl adipate and cyclopentasiloxane.

17. The anhydrous topical sunscreen composition of claim 16, wherein said solvent mixture consisting essentially of isododecane and cyclopentasiloxane.

18. The anhydrous topical sunscreen composition of claim 16 wherein said water insoluble film forming polymers comprise trimethylsiloxysilicate in an amount of 0.5 to 3 wt. %, and acrylate/dimethicone copolymer in an amount of 0.2 to 3 wt. %, based on a total weight of the composition.

19. The anhydrous topical sunscreen composition of claim 16 wherein said water insoluble film forming polymers comprise trimethylsiloxysilicate in an amount of 0.5 to 3 wt. %, and methyl dihydroabietate, based on a total weight of the composition.

* * * * *